(12) United States Patent
Meyer-Kobbe et al.

(10) Patent No.: US 9,555,158 B2
(45) Date of Patent: Jan. 31, 2017

(54) NICKEL-FREE IRON ALLOY FOR STENTS

(71) Applicant: MeKo Laserstrahl-Materialbearbeitungen e.K, Sarstedt (DE)

(72) Inventors: Clemens Meyer-Kobbe, Sarstedt (DE); Mark Rosentreter, Neustadt (DE)

(73) Assignee: MeKo Laserstrahl-Materialbearbeitungen e.K, Sarstedt (DE)

( * ) Notice: Subject to any disclaimer, the term of this patent is extended or adjusted under 35 U.S.C. 154(b) by 238 days.

(21) Appl. No.: 14/373,065

(22) PCT Filed: Jan. 15, 2013

(86) PCT No.: PCT/EP2013/050652
§ 371 (c)(1),
(2) Date: Jul. 18, 2014

(87) PCT Pub. No.: WO2013/107730
PCT Pub. Date: Jul. 25, 2013

(65) Prior Publication Data
US 2014/0364960 A1    Dec. 11, 2014

Related U.S. Application Data

(60) Provisional application No. 61/633,324, filed on Feb. 9, 2012.

(30) Foreign Application Priority Data

Jan. 18, 2012    (EP) .................................... 12151650

(51) Int. Cl.
| C22C 38/38 | (2006.01) |
| C22C 38/22 | (2006.01) |
| A61L 27/04 | (2006.01) |
| C21D 6/00  | (2006.01) |
| C22C 38/18 | (2006.01) |
| A61L 31/02 | (2006.01) |
| A61F 2/82  | (2013.01) |
| C22C 38/00 | (2006.01) |
| C22C 38/02 | (2006.01) |
| C22C 38/44 | (2006.01) |
| C22C 38/58 | (2006.01) |

(52) U.S. Cl.
CPC ................ *A61L 27/042* (2013.01); *A61F 2/82* (2013.01); *A61L 27/047* (2013.01); *A61L 31/022* (2013.01); *C21D 6/002* (2013.01); *C22C 38/001* (2013.01); *C22C 38/02* (2013.01); *C22C 38/18* (2013.01); *C22C 38/38* (2013.01); *C22C 38/44* (2013.01); *C22C 38/58* (2013.01)

(58) Field of Classification Search
None
See application file for complete search history.

(56) References Cited

U.S. PATENT DOCUMENTS

| 5,714,115 | A   | 2/1998 | Speidel et al. |
| 6,267,921 | B1  | 7/2001 | Montagnon |
| 2007/0166496 | A1* | 7/2007 | Kramer ................. A61L 27/306 428/36.9 |
| 2011/0226391 | A1* | 9/2011 | Kim ......................... C21D 1/18 148/542 |

FOREIGN PATENT DOCUMENTS

GB          778597       *   7/1957

OTHER PUBLICATIONS

International Search Report for PCT/EP2013/050652 mailed on Feb. 18, 2013.
Written Opinion for PCT/EP2013/050652 mailed on Feb. 18, 2013.

* cited by examiner

*Primary Examiner* — Deborah Yee
(74) *Attorney, Agent, or Firm* — Amin, Turocy & Watson LLP

(57) ABSTRACT

The present invention is directed to a largely nickel-free iron alloy or a nickel-free stainless steel having the following composition:

| 14.0% by wt.-16.5% by wt.  | chromium |
| 10.0% by wt.-12.0% by wt.  | manganese |
| 3.0% by wt.-4.00% by wt.   | molybdenum |
| 0.55% by wt.-0.70% by wt.  | nitrogen |
| 0.10% by wt.-0.20% by wt.  | carbon |
| 0.00% by wt.-2.00% by wt.  | impurities, such as other metals, semimetals, metal salts and/or non-metals | the rest up to 100% by wt. is iron, which is in particular suitable for the production of stents as well as to stents made of this alloy.

8 Claims, No Drawings

NICKEL-FREE IRON ALLOY FOR STENTS

The present invention is directed to a largely nickel-free iron alloy or a nickel-free stainless steel, which is in particular suitable for the production of stents, and to stents made thereof.

Nowadays, the implantation of vessel supports such as for example stents is a common surgical procedure for the treatment of stenoses. They are usually made of metal alloys such as stainless steel or nitinol. Such metal stents are known in large numbers and have proven themselves in practice. Due to their metallic structure and load capacity such metal stents shall guarantee that the vessels remain open after implantation and that the blood flow through the vessels will be guaranteed permanently. On the other hand, stents are used in the treatment of cancer in order to keep open after a dilation restrictions of respiratory tracts (trachea), biliary tracts or of the esophagus caused by malignant tumors.

A stent is a small lattice framework in the shape of a small tube. It is advanced via a catheter to the position, where a blood vessel is constricted by arteriosclerosis. There the lattice framework is pressed from the inside against the vessel wall by means of a balloon. The wall is widened and the constriction is dilated. Herein, the stent should ensure that the artery cannot constrict any longer, a risk that is due to the elastic restoring force of a vessel wall. Over time, the cells of the vessel wall grow around the stent so that it is a support within the artery. However, this can be delayed by occurring inflammatory reactions.

The human body can develop a hypersensitivity reaction, especially allergies, upon contact with certain substances. Here, this is an overshooting defense reaction of the immune system to certain environmental substances (allergens), which is often accompanied by inflammatory processes. Thus, also the danger of a perturbation of wound healing exists, which is accompanied by an increased risk of thrombosis. The exposure-related symptoms of an allergy can be mild to severe and in some cases even acutely life-threatening. Nickel is nowadays one of the most common contact allergens.

Stainless steels of the prior art (e.g. 18/10 CrNi, 316L) contain to a large degree nickel. Therefore, they can cause a nickel allergy upon contact with the human body. Thus, there are legislative measures in various European countries which limit or prohibit the use of nickel-containing materials on or in the human body. The European Directive 94/27/EG establishes for example a threshold value for the release of nickel for products that come into direct and prolonged contact with the skin.

Cobalt is a widely distributed contact allergen as well, that can cause a hypersensitivity reaction or allergy in an exposure-related manner similar to nickel. Cobalt is the main component of cobalt-chromium alloys, which are used for the production of stents due to their excellent mechanical properties. However, these can cause an allergy upon contact with the human body, in many cases this occurs as a cross reaction with an allergy to nickel. It is assumed that one third of all persons suffering from an allergy to nickel also show reactions to cobalt.

The patent U.S. Pat. No. 6,508,832 discloses stents made from the nickel-free stainless steel Bio Dur® 108 of Carpenter Technologies, USA. Though in experiments of the inventors of this application the yield strength of this alloy ($R_{p0.2}$~800 MPa) was so high that this alloy has a large elastic deformability in combination with a relatively low modulus of elasticity (~195 GPa). If the stent made of this alloy is routinely crimped onto a catheter balloon, it springs back elastically (Spring Back), so that the stent is not seated strong enough on the balloon and can slip off the balloon during the implantation.

The patent application EP 640 695 A1 discloses a nickel-free, austenitic alloy for the production of products having skin contact. The composition of the alloy according to EP 640 695 A1 contains the same elements as the present invention, but differs in particular in the nitrogen and carbon content. However, implants and particularly stents made of this alloy are not described.

The patent application EP 1 087 029 A2 is directed to nickel-free steel alloys for medical implants, but not specifically stents. The composition of the alloy from EP 1 087 029 A2 differs from the composition of the alloy of the present invention most notably due to the lower mass of molybdenum, which has been proven to be sparsely suitable for the production of stents. Furthermore, the European patent application EP 0 875 591 B1 discloses the use of an austenitic steel alloy for the production of items that are worn on or in the body. Here, at a nitrogen content of more than 0.55% the carbon content has to be >0.3%. However, this has proven to be unfavorable for the production of stents.

The German patent DE 195 13 407 C1 describes the use of an austenitic steel alloy for the production of items worn on or in the body. Stents made from this alloy are not described. The present alloy is a purposeful selection of the alloying elements as well as of their amounts used, which lead to a composition optimally suited for stents.

Objective of the present invention is to provide a largely nickel-free iron alloy which is particularly suitable for the production of stents.

According to the invention said objective is solved by the technical teaching of the independent claims. Further advantageous embodiments of the invention result from the dependent claims, the description as well as the examples.

It has surprisingly been shown that the inventive nickel-free steel alloys are characterized by an advantageous corrosion behavior, desired strength and further mechanical properties suitable for the production of stents. In addition, these alloys cannot cause nickel allergies due to the uncritical concentration of nickel.

The present invention is therefore directed to, among others, a steel alloy, preferably an austenitic steel alloy, containing the following components based on the total weight of the alloy (specified as % by wt.):

| | |
|---|---|
| 14.00% by wt.-16.50% by wt. | chromium |
| 10.00% by wt.-12.00% by wt. | manganese |
| 3.00% by wt.-4.00% by wt. | molybdenum |
| 0.55% by wt.-0.70% by wt. | nitrogen |
| 0.10% by wt.-0.20% by wt. | carbon |
| the rest up to 100% by wt. is iron. | |

This alloy can additionally contain impurities. If also other components apart from chromium, manganese, molybdenum, nitrogen and carbon are present, so these are impurities such as for example other metals, metal salts, non-metals, sulfur, oxygen, silicon and/or hydrogen. The impurities existent in the alloy are production-related impurities.

The present invention provides a substantially nickel-free iron alloy, which is particularly suitable for the production of stents and is superior to the iron alloys known in the prior art, because the effects of the individual alloy components as such as well as in relation to the other components have been studied in detail, and optimal ranges and threshold values were determined for each alloy component, which all taken together give the alloy superior properties.

Thus, the amount of manganese has been limited to a small but advantageous range, which does not correspond to the preferred range in EP 640 695 A1. Moreover, EP 640 695 A1 discloses alloys with a low proportion of molybdenum, which has been proven to be unsuitable in respect of the inventive alloy due to the corrosion resistance. With regard to the yield strength a low content of nitrogen is preferred. In the context of the present invention, it has also been found that a higher content of carbon is necessary to achieve the mechanical properties of a nitrogen-reduced, nickel-free steel alloy, which are required for stents. This optimization of a nickel-free steel alloy as material for stents cannot be learned from any of the previously described patent specifications. In particular, the amounts of nitrogen and carbon used in the examples of DE 195 13 407 C1 are in a range which, as shown in this application, has an adverse effect on the mechanical properties of the alloy.

The European patent EP 1 025 273 B1 discloses a nickel-free, austenitic alloy for the production of products with body contact. The alloys from EP 1 025 273 B1 differ from the present invention most notably in the amount of manganese which is considerably higher (>15%). However, as shown in the examples of this application, nickel-free steel alloys with a higher manganese content do not have the mechanical properties desired for stents.

The patent application EP 1 579 886 A1 describes medical devices, also stents, made of a nickel-free iron alloy. The applicants of EP 1 579 886 A1 examined mainly the influence of nitrogen in a nickel-free alloy and preferred a minimum content of 0.8% by wt. This was tested by checking the strength of a particular composition with and without nitrogen. The subject-matter of this application is however based on developing an optimized composition by matching the amounts of all components to each other. This led to better suited narrower subranges of the larger ranges of EP 1 579 886 A1, which in addition differ most notably from the preferred ranges in the prior art in the manganese and nitrogen content. For example, in the alloy tested in EP 1 579 886 A1 absolutely no manganese was contained and the nitrogen content was higher.

The authors of the scientific publication: Chen et al., Computational Materials Science, 2009; 572-578 examined the ratcheting and fatigue properties of an X13CrMnMoN18-14-3 alloy. The result of the present invention shows however, that it is advantageous for the mechanical properties, if the composition of an alloy is changed concerning these matters. Both the chromium and the manganese proportion and in particular the nitrogen content should be lower in order to produce a yield strength optimal for the use as material for stents.

The large restoring forces of the vessels after a dilation and inflammatory reactions are the main reasons for restenoses. Therefore, in particular vascular vessel supports or stents must be made of a material, which is tolerated well by the body, i.e. does not cause allergies or intolerances, but also has a sufficiently high retention force and stability to prevent a renewed occlusion of the vessel.

A stent once inserted must maintain its size and shape, despite the different forces acting on it, such as the pulsating load by the beating heart. In addition, the stent must have enough flexibility in order to be able to be crimped onto a balloon and later to be expanded inside the vessel.

For this reason, there is the need to develop a suitable, nickel-free material for stents. The object of the present invention is to provide an especially well suited material, and a vessel support made thereof.

The alloy according to the invention can contain production-related impurities such as for example further metals, semimetals, metal salts and/or non-metals in small amounts up to maximally 2.0% by wt. of all further components together. The further components are preferably nickel, titanium, niobium, silicon, sulfur and phosphorus, wherein the upper limit for nickel is at 0.05-% by wt. in the alloy. Titanium and niobium can be contained in the alloy each in an amount of up to 0.07% by wt., preferably 0.05% by wt. and in particular preferably 0.02% by wt. Silicon can be present in the alloy in an amount of up to 0.1% by wt. and preferably 0.50% by wt. and phosphorus in an amount of up to 0.05% by wt. The total amount of impurities apart from chromium, manganese, molybdenum, nitrogen, carbon and iron should in total not exceed 2.0% by wt., preferably 1.6% by wt., more preferably 1.4% by wt., even more preferably 1.2% by wt., even more preferably 1.1% by wt., and most preferably 1.0% by wt.

It goes without saying that all components of an alloy must have together 100% by wt. If the above alloy contains thus 16.5% by wt. chromium (Cr) and 12.0% by wt. manganese (Mn) as well as 4.0% by wt. molybdenum (Mo), 0.70% by wt. nitrogen (N) and 0.20% by wt. carbon (C), then the proportion of iron (Fe) cannot lie above 66.60% by wt.

Unless specifically listed, the herein disclosed alloys can contain production-related impurities, which are in the range of the detection limit or in the range of 1 ppm up to 2.0% by wt., preferably up to 1.8% by wt., more preferably up to 1.5% by wt., and in particular preferably up to 1.2% by wt. Herein, silicon as the main component of the impurities can already represent up to 1.0% by wt., preferably up to 0.9% by wt. It is therefore particularly preferred, if the production-related impurities except for silicon are in total less than 1.0% by wt., preferably less than 0.8% by wt., more preferably less than 0.5% by wt., more preferably less than 0.2% by wt., more preferably less than 0.1% by wt., more preferably less than 0.05% by wt., more preferably less than 0.01% by wt. and in particular preferably less than 500 ppm. The aforementioned percentages are based on the sum of all impurities except for silicon and not on the individual impurity. These impurities (inclusive Si) can also be present in the alloy in an amount of 1 ppm up to 2.0% by wt. or 1.8% by wt. or 1.5% by wt. or 1.2% by wt. if they are not explicitly indicated as alloy component and in the case of non-indication are ascribed to the weight proportion of the component of the alloy through which they entered the alloy. However, it is preferred, if the impurities except for silicon each, i.e. based on the individual element, do not exceed an amount of 0.1% by wt., more preferred 0.05% by wt., more preferred less 0.01% by wt., preferred 500 ppm, more preferred 300 ppm and particularly preferred 150 ppm. Silicon can be a main component of the impurities and be present in the alloy up to 1.0% by wt. and preferably up to 0.8% by wt.

The invention further comprises steel alloys consisting of the following components based on the total weight of the alloy:

---

14.0% by wt.-16.5% by wt. chromium
10.0% by wt.-12.0% by wt. manganese

| | |
|---|---|
| 3.0% by wt.-4.0% by wt. | molybdenum |
| 0.55% by wt.-0.70% by wt. | nitrogen |
| 0.10% by wt.-0.20% by wt. | carbon |
| 1 ppm.-2.0% by wt. | impurities in form of other metals (i.e. others than chromium, manganese, molybdenum and iron) each in a maximum amount of up to 0.075% by wt., and non-metals from the group of S, Si, P in a maximal total amount of 1.2% by wt., the rest up to 100% by wt. is iron. |

The term "non-metals from the group of S, Si, P in a maximal total amount of 1.2% by wt." means that the proportion of sulfur, phosphorus and silicon together does not exceed the maximum amount of 1.2% by wt., wherein it is preferred that silicon represents up to 1.0% by wt. and sulfur and phosphorus together do not contribute more than 0.2% by wt.

It is preferred, if the alloys according to the invention are austenitic steel alloys. A preferred composition of a steel alloy according to the invention further contains apart from chromium, manganese, molybdenum, nitrogen, carbon 0.00% by wt.-0.05% by wt. nickel and/or 0.00% by wt.-1.00% by wt. silicon.

A preferred composition of a steel alloy according to the invention consists of the following components based on the total weight of the alloy:

| | |
|---|---|
| 14.0% by wt.-16.5% by wt. | chromium |
| 10.0% by wt.-12.0% by wt. | manganese |
| 3.0% by wt.-4.0% by wt. | molybdenum |
| 0.55% by wt.-0.70% by wt. | nitrogen |
| 0.10% by wt.-0.20% by wt. | carbon |
| 0.00% by wt.-2.00% by wt. | impurities, such as other metals, semimetals and/or other non-metals |
| and the rest up to 100% by wt. is iron. | |

It is even more preferred, if the composition of the steel alloy according to the invention consists of the following components based on the total weight of the alloy:

| | |
|---|---|
| 14.0% by wt.-16.5% by wt. | chromium |
| 10.0% by wt.-12.0% by wt. | manganese |
| 3.0% by wt.-4.0% by wt. | molybdenum |
| 0.55% by wt.-0.70% by wt. | nitrogen |
| 0.10% by wt.-0.20% by wt. | carbon |
| 0.00% by wt.-0.05% by wt. | nickel |
| 0.00% by wt.-1.00% by wt. | silicon (further preferred up to 0.5% by wt.) |
| 0.00% by wt.-1.00% by wt. | impurities, such as other metals, semimetals and/or other non-metals (further preferred up to 0.5% by wt.) |
| and the rest up to 100% by wt. is iron. | |

In the aforementioned alloy, the other metals (i.e. others than chromium, manganese, molybdenum, nickel and iron) are preferably contained each in a maximum amount of 0.05% by wt. and the other non-metals (i.e. others than nitrogen, carbon and silicon) each in a maximum amount of 0.05% by wt. in the aforementioned alloy.

The steel alloy according to the invention contains 0.10% by wt.-0.20% by wt. carbon. It is preferred that a steel alloy according to the invention contains 0.12% by wt.-0.20% by wt. and more preferred 0.14% by wt.-0.19% by wt. and even more preferred 0.16% by wt.-0.18% by wt. carbon based on the total weight of the alloy.

It is additionally preferred, if the mass of C and N together is more than 0.70% by wt., more preferred more than 0.75% by wt., even more preferred more than 0.80% by wt. and even more preferred between 0.80% by wt. and 0.90% by wt. and particularly preferred between 0.83% by wt. and 0.87% by wt.

At high contents chromium promotes the formation of delta ferrite and sigma phases and reduces the austenitic region; this is why the chromium content must be limited. However, a chromium content of 17.00% by wt. and more has been proven to be unsuitable for the inventive alloy. On the other hand, chromium increases the corrosion resistance, the nitrogen solubility and improves the polishability so that chromium represents nevertheless an important component of the alloy.

It is thus preferred, if the alloy according to the invention has 14.0-16.5% by wt., preferably 14.5-16.3% by wt., more preferably 14.8-16.2% by wt., more preferably 15.0-16.1% by wt., even more preferably 15.2-16.0% by wt. chromium.

At high contents manganese forms intermetallic phases that reduce the corrosion resistance and lead to the embrittlement of the material. Furthermore, a high content of manganese, due to the high chemical activity, leads to a poor polishability. In the prior art, iron alloys with a manganese content of much more than 18% by wt. are known. These alloys were also tested for comparison purposes and have proven to be not applicable, also due to the poor polishability.

The so-called MARC value (Measure of Alloying for Resistance to Corrosion) is the latest approach to calculate the chemical resistance. It is based on the PRE value (Pitting Resistance Equivalent) and is extended by the elements carbon, manganese and nickel.

$$MARC=[\% \ Cr]+3.3\times[\% \ Mo]+20\times[\% \ C]+20\times[\% \ N]-0.5\times[\% \ Mn]-0.25[\% \ Ni]$$

By reference to the formula for the MARC value, it is evident that manganese reduces the corrosion resistance.

The following formula represents among other things, the impact of manganese on the yield strength:

$$\text{Yield strength(MPa)}=251+33\times Mn(m\ \%)+313\times[N+C(m\ \%)]$$

The yield strength is increased by 33 MPa by the addition of 1% manganese. The reduction of the corrosion resistance and the increase of the yield strength by the addition of manganese suggest a low manganese content. On the other hand, manganese increases the nitrogen solubility and enlarges the austenite area. This argues for a high manganese content.

Preferably, the mass of manganese is therefore in the range of 10.0-12.0% by wt., more preferably 10.2-11.9% by wt., more preferably 10.5-11.9% by wt., even more preferably 10.8-11.8% by wt., more preferably 10.3-11.6% by wt. and especially preferably of 11.0-11.7% by wt.

It is additionally preferred, if the alloy according to the invention contains molybdenum in proportions of 3.0-4.0% by wt., more preferred 3.1-3.8% by wt. and especially preferred of 3.2-3.7% by wt.

Molybdenum increases the resistance to pitting corrosion in reducing environments and was therefore selected as a component of the alloy. Molybdenum promotes the formation of alpha phases and sigma phases and deteriorates the polishing result due to its high passivation. Furthermore, molybdenum is a strong ferrite former. Due to the strong deformation process during the crimping (fitting of the stent onto a catheter balloon) and dilatation also austenitic materials become partly ferritic. Therefore, the material should be as far away as possible from the transition point to the ferritic material by use of austenite-promoting alloying elements and avoidance of ferrite-promoting alloying elements. Molybdenum is a strong carbide former. The formation of carbides is dependent on the carbon content, on the content of the carbide former and on the heat treatment in dependence of the condition of the material, such as for example the dislocation density, before the heat treatment. In order to achieve the desired elongation at break, a large change of the structural conditions is necessary, which leads to an increased disposition to form carbides. For a use as a stent material carbides in an alloy are of disadvantage, since inhomogeneities of the material promote crack formation, lead to unpolished spots on the stent and to a local depletion of carbon and thereby reduce the corrosion resistance and the strength. In this respect, the molybdenum content in the alloys according to the invention should be limited to 4.0% by wt.

With an increase of the nitrogen content, the probability increases that nitrides, such as e.g. chromium nitrides, are formed. This reduces the corrosion resistance due to the surrounding depletion of chromium and nitrogen. Therefore, in context of this invention an upper limit of the nitrogen content should be determined in a steel alloy according to the invention (see example 7). Since the nitride formation depends also on the heat treatment parameters, the nitrogen content must be selected in dependence on the applied heat treatment. Nitrogen increases the strength of the alloy. In the use as a stent, especially as a vascular stent, a low elastic elongation is required, since the stent is crimped onto a balloon. If the implant springs back strongly after crimping (Spring Back), it can slip off the balloon during the implantation. To achieve a low elastic deformation at the given modulus of elasticity, a low yield strength ($R_{p0.2}$), preferred lower than 600 MPa, has thus to be generated. The yield strength can be adjusted in certain ranges by a suitable heat treatment process and on the other hand by a low nitrogen content.

Atomically dissolved nitrogen increases the chemical resistance so that a sufficient chemical resistance of a steel alloy without the addition of nickel becomes only then possible. Therefore, a minimum content of nitrogen is required. Furthermore, nitrogen is a strong austenite former so that a minimum content is necessary to ensure an austenitic structure of the steel alloy.

The yield strength of steel alloys increases with a higher nitrogen content. Because the yield strength has to be lower than 600 MPa for the use as a stent, a nitrogen content as low as possible is demanded in regard to the yield strength.

It is thus preferred that the alloy according to the invention has 0.50-0.70% by wt., preferably 0.55-0.70% by wt., preferably 0.58-0.69% by wt., more preferably 0.60-0.68% by wt. and still more preferably 0.62-0.67% by wt., even more preferably 0.55-0.61% by wt. and still especially preferred 0.56-0.59% by wt. nitrogen.

Due to a suitable heat treatment process, carbon, as nitrogen, occupies interstitial sites and thereby increases the strength and enlarges the austenite area in a steel alloy. The increase in strength by carbon is, however, lower than that by nitrogen. Typically, the carbon content in austenitic steels is still severely limited (e.g. to <0.06% by wt. or even <0.03% by wt.) in order to avoid the formation of carbides such as chromium carbide, since such precipitations lead to a depletion of chromium in the surrounding material and therefore to a reduced corrosion resistance.

In order to prevent the very poorly avoidable small proportion of carbon from entering into a connection with chromium, the carbon is bound in the prior art to other elements, which are added to a small extent to the alloy for this purpose. Elements which are typically added to the alloy due to their high affinity to carbon are titanium, niobium and vanadium. Known austenitic alloys thus have no atomically dissolved carbon.

In the context of the alloy composition according to the invention the formation of chromium carbide can be avoided by an appropriate temperature control, which can be conducted in this manner only on very thin-walled structural components.

During the production process of an alloy carbon can increasingly form a bond with tungsten and thereby reduces the proportion of free, atomic carbon. The carbides arising in this manner cannot be dissolved by a heat treatment. Therefore, the alloys according to the invention shall preferably be free of tungsten or the tungsten content of an alloy according to the invention shall be limited to ≤0.05% by wt. and preferably ≤0.02% by wt., in particular preferably 500 ppm, more preferably 300 ppm and in particular preferably 150 ppm.

The steel alloy according to the invention has a carbon content of 0.10% by wt. to 0.20% by wt. The content of titanium, niobium and vanadium is preferably limited each to a maximum of 0.02% by wt. in order to prevent a carbon compound with these elements. In this way, it is ensured that the carbon is present, at least in substantial parts, in atomic form. In the alloys according to the invention carbon is present preferably to at least 70% by wt. in free, i.e. atomic form and not bound as carbide and more preferably to at least 80% by wt. and even more preferably to at least 90% by wt. in free or atomic form.

The actual lattice structure can be determined by means of X-ray structure analysis. For this, X-rays are diffracted at the crystal lattice, so that interference patterns arise. From these interference patterns one can conclude on the atomic distances. The atomic distances are influenced by atomically dissolved carbon and nitrogen, but not by incoherent precipitations of bound carbon or nitrogen. Thus, in case of a known total content of carbon and nitrogen and by determination of the atomically dissolved carbon and nitrogen by means of the X-ray structure analysis, the ratio of atomically dissolved carbon and nitrogen and bound carbon and nitrogen can be determined In the presence of completely dissolved nitrogen completely dissolved carbon has other positive properties than in the absence of nitrogen, so that advantages for the alloy are produced due to the superimposed effect of the two elements. This positive effect applies to the chromium-manganese steels studied here and is maybe not transferable to other alloys. Furthermore, it was found that a certain ratio of nitrogen to carbon enhances the positive properties. In order to dissolve both carbon and nitrogen completely in an alloy the chromium and manganese content has to be adjusted accordingly and preferably a heat treatment adapted to the given conditions, such as wall thickness and present dislocation density, has to be carried out.

In contrast to nitrogen, carbon increases the elongation at break and uniform elongation. Furthermore, carbon avoids the formation of delta ferrite more effectively than nitrogen. In addition, carbon stabilizes austenite stronger than nitrogen.

In comparison to nitrogen, carbon generates a smaller increase of strength both in the tensile strength $R_m$, and also in yield strength $R_{p0.2}$. Due to a larger lattice distortion, a much larger short-range order effect and due to a significantly more effective grain-boundary strengthening, nitrogen leads to higher strengths. The smaller effect of the carbon on the grain-boundary strengthening has particular importance for the use according to the invention, because both a fine grain and a low yield strength are required and these conflicting requirements become compatible at a sufficiently high capability of repassivation only with the addition of carbon.

Carbon increases, comparable to nitrogen, the general corrosion resistance. However, the capability of repassivation is increased to a special degree by the addition of carbon. The capability of repassivation of stents, in particular of vascular implants, is of particular importance, because the passivation layer is destroyed during the insertion of an implant and the surfaces must repassivate in the oxygen-deficient (oxygen-deficient regarding to chemically non-bound oxygen) as well as corrosive medium blood.

In summary it can be stated, that a replacement of a portion of the nitrogen content by carbon is advantageous for the use as a stent, and in particular as a vascular vessel support, both from the mechanical point of view by increasing the uniform elongation and elongation at break as well as by a reduction of the strength, and from the chemical point of view by increasing the potential of repassivation.

Furthermore, the formation of delta ferrite is prevented. However, the high binding affinity of carbon imposes increased metallurgical requirements, since titanium, niobium and vanadium should preferably only be present at very low contents of each less than 0.02% and the carbon content has to be adjusted accurately.

Furthermore, it is advantageous to accomplish the parameters of the heat treatment, which consists of the heating rates, the cooling rates, the holding times and the prevailing atmospheres, in such a manner that in dependence on the actual strain hardenings and dimensions of the structural component the formation of carbides can be excluded.

Preferably, the mass of carbon is in the range of 0.10-0.20% by wt., preferably at 0.12-0.20% by wt., more preferably 0.13-0.19% by wt., even more preferably 0.14-0.18% by wt. and in particular preferably of 0.15-0.17% by wt.

Furthermore, it is preferred, when the sum of the weight proportions of nitrogen and carbon in the alloy is 0.7-0.90% by wt., more preferred 0.72-0.88% by wt. and even more preferred 0.73-0.86% by wt. and particularly preferred 0.74-0.84% by wt.

In addition, it is preferred, when the ratio of the % by wt. of nitrogen and carbon is in the following ranges: N:C from 3.0 to 6.6, preferred N:C from 3.3 to 6.3 and more preferred N:C from 3.5 to 6.0.

At the ratio of N:C in the range from 3.5 to 6.0 the most pronounced positive effects were found. By which means these effects are caused is not known in detail yet. It is assumed that by precipitation effects a higher carbon proportion overcompensates the positive effect of the atomically dissolved carbon especially on the repassivation behavior.

In addition to the aforementioned components, a steel alloy according to the invention can additionally contain apart from silicon also 0.0% by wt.-1.1% by wt., preferably 0.1% by wt.-0.6% by wt., more preferably 0.2% by wt.-0.4% by wt. impurities such as other metals, metal salts, nonmetals, sulfur, phosphorus, oxygen and/or hydrogen. These further components are mostly production-related impurities which are harmless for the product properties or the properties of the alloy in the aforementioned small amounts. However, it is preferred that the metal copper (Cu) is present below 300 ppm, preferably below 200 ppm and more preferably below 150 ppm.

Furthermore, it is preferred, that the proportions of the metals vanadium and cobalt are each ≤0.02% by wt, preferably ≤0.01% by wt., more preferably ≤0.005% by wt.

A preferred composition of a steel alloy according to the invention comprises or consists of:

16.0% by wt. chromium
12.0% by wt. manganese
3.19% by wt. molybdenum
0.62% by wt. nitrogen
0.15% by wt. carbon
<0.03% by wt. nickel
up to 0.10% by wt. impurities, such as
other metals and/or other non-metals
up to 100% by wt. iron.

An additional preferred composition of a steel alloy according to the invention comprises or consists of:

16.5% by wt. chromium
10.0% by wt. manganese
3.60% by wt. molybdenum
0.68% by wt. nitrogen
0.17% by wt. carbon
<0.03% by wt. nickel
up to 0.10% by wt. impurities, such as
other metals and/or other non-metals
up to 100% by wt. iron.

An additional preferred composition of a steel alloy according to the invention comprises or consists of:

16.05% by wt. chromium
12.0% by wt. manganese
3.21% by wt. molybdenum
0.63% by wt. nitrogen
0.14% by wt. carbon
0.06% by wt. nickel
0.82% by wt. silicon
up to 0.10% by wt. impurities, such as
other metals and/or other non-metals
up to 100% by wt. iron.

All "% by wt." specified in this application are based on the total weight of the respective alloy. Thus, it is valid for all compositions listed herein that the sum of all components must result together in 100.00% by wt. This means that after addition of all listed components of the iron alloy the difference to 100% by wt. consists of iron as the main component. In addition, these compositions can also contain a very small amount of partially unavoidable, production-related impurities. If the amount of the impurities is not explicitly quoted, it is preferred that these impurities are each ≤0.2% by wt., in particular ≤0.02% by wt. and in sum of all impurities ≤1.0% by wt., more preferably ≤0.6% by wt.

Furthermore, the present invention comprises preferably steel alloys which do not contain further components apart from iron, chromium, manganese, molybdenum, nitrogen, carbon, and unavoidable production-related impurities such as nickel, phosphorus, silicon and sulfur. This means, it is preferred, if the components of the alloy, apart from the basis iron, are selected from the following group comprising or consisting of: chromium, manganese, molybdenum, nitrogen, carbon and unavoidable production-related impurities. It is particularly preferred that the alloys according to the invention do not contain copper. Since copper leads not only to increased apoptosis, but also to necrotic cell death with symptoms of inflammation and abscesses, the copper content shall be limited as far as technically possible and not account for more than 0.02% by wt. and further preferred not for more than 500 ppm, further preferred not for more than 300 ppm and particularly preferred not for more than 150 ppm. It is reported that even the lowest copper contents of $0.1 \times 10^{-3}$ mol have a proliferation-inhibiting effect. This effect can be desirable for some applications in which the ingrowth of the implant or at least parts of the implant is undesirable. Joint surfaces of artificial joints are to be mentioned here exemplarily. In the use as vascular stent, however, a persistent inhibition of proliferation has the major disadvantage that the stent remains in direct contact with the blood, and also a long time after the introduction of the stent a thrombosis may occur. Due to the resulting high mortality rate a thrombosis is to be prevented as far as possible. Hence, also traces of copper must be reduced as far as technically possible.

Comparable to nickel, also cobalt is known as a common contact allergen, so that the amount of cobalt in the alloy should be reduced to the minimum technically possible. It is therefore especially preferred that the alloys according to the invention contain no cobalt. At least, the maximal amount of cobalt in one of the alloys according to the invention shall be ≤0.2% by wt., preferably ≤0.05% by wt., preferably ≤0.02% by wt. and more preferably ≤500 ppm, more preferably ≤300 ppm and in particular preferably ≤150 ppm.

In steel alloys vanadium forms especially stable carbides, which should preferably be avoided in accordance with the invention. In addition, vanadium carbide is classified as being carcinogenic and mutagenic to germ cells, each in class 2. Thus, it is especially preferred that the alloys according to the invention contain no vanadium. At least, the maximal amount of vanadium in one of the alloys according to the invention shall be ≤0.2% by wt., preferably ≤0.05% by wt. and more preferably ≤0.02% by wt., preferably ≤500 ppm, more preferably ≤300 ppm and in particular preferably ≤150 ppm.

Stents coated with gold have yielded worse results than uncoated steel stents in clinical trials, so that the alloy according to the invention shall contain no gold. Preferably, the gold content in one of the alloys according to the invention shall thus be ≤0.2% by wt., more preferably ≤0.05% by wt. and still more preferably ≤0.02% by wt. and more preferably ≤500 ppm, more preferably ≤300 ppm and in particular preferably ≤150 ppm.

If apart from iron, chromium, manganese, molybdenum, nitrogen, carbon production-related impurities are contained in the alloy, then these production-related impurities are other metals, metal salts, non-metals, silicon, sulfur, nickel, titanium, niobium, phosphorus and/or hydrogen, which are present in small amounts of <2.00% by wt., preferably <1.10% by wt., preferably <0.80% by wt., more preferably <0.60% by wt., more preferably <0.50% by wt., more preferably <0.40% by wt., more preferably <0.30% by wt., more preferably <0.20% by wt. and in particular preferably <0.10% by wt.

As "other metals", which may be present in the composition of the iron alloy according to the invention, the following are to be mentioned:
beryllium, sodium, aluminum, potassium, calcium, scandium, titanium, magnesium, gallium, niobium, technetium, ruthenium, rhodium, palladium, silver, indium, dysprosium, neodymium, gallium, gadolinium, yttrium, lithium, zinc, zirconium, tin, lanthanum, cerium, praseodymium, promethium, samarium, terbium, holmium, erbium, thulium, lutetium, tantalum, rhenium, platinum and lead. Furthermore, metal salts may be contained in very small amounts as impurities in the alloy.

Metal salts preferably contain at least one of the following metal ions: $Be^{2+}$, $Na^+$, $Mg^{2+}$, $K^+$, $Ca^{2+}$, $Sc^{3+}$, $Ti^{2+}$, $Ti^{4+}$, $Cr^{2+}$, $Cr^{3+}$, $Cr^{4+}$, $Cr^{6+}$, $Mn^{2+}$, $Mn^{3+}$, $Mn^{4+}$, $Mn^{5+}$, $Mn^{6+}$, $Mn^{7+}$, $Fe^{2+}$, $Fe^{3+}$, $Ni^{2+}$, $Zn^{2+}$, $Al^{3+}$, $Zr^{2+}$, $Zr^{4+}$, $Nb^{2+}$, $Nb^{4+}$, $Nb^{5+}$, $Mo^{4+}$, $Mo^{6+}$, $Tc^{2+}$, $Tc^{3+}$, $Tc^{4+}$, $Tc^{5+}$, $Tc^{6+}$, $Tc^{7+}$, $Ru^{3+}$, $Ru^{4+}$, $Ru^{5+}$, $Ru^{6+}$, $Ru^{7+}$, $Ru^{8+}$, $Rh^{3+}$, $Rh^{4+}$, $Pd^{2+}$, $Pd^{3+}$, $Ag^+$, $In^+$, $In^{3+}$, $Ta^{4+}$, $Ta^{5+}$, $Pt^{2+}$, $Pt^{3+}$, $Pt^{4+}$, $Pt^{5+}$, $Pt^{6+}$, $Au^+$, $Au^{3+}$, $Au^{5+}$, $Sn^{2+}$, $Sn^{4+}$, $Pb^{2+}$, $Pb^{4+}$, $La^{3+}$, $Ce^{3+}$, $Ce^{4+}$, $Gd^{3+}$, $Nd^{3+}$, $Pr^{3+}$, $Tb^{3+}$, $Pr^{3+}$, $Pm^{3+}$, $Sm^{3+}$, $Eu^{2+}$, $Dy^{3+}$, $Ho^{3+}$, $Er^{3+}$, $Tm^{3+}$.

Halogens such as $F^-$, $Cl^-$, $Br^-$, oxides and hydroxides such as $OH^-$, $O^{2-}$, sulfates, carbonates, oxalates, phosphates such as $HSO_4^-$, $SO_4^{2-}$, $HCO_3^-$, $CO_3^2$, $HC_2O_4^-$, $C_2O_4^{2-}$, $H_2PO_4^-$, $HPO_4^{2-}$, $PO_4^{3-}$, and especially carboxylates such as $HCOO^-$, $CH_3COO^-$, $C_2H_5COO^-$, $C_3H_7COO^-$, $C_4H_9COO^-$, $C_5H_{11}COO^-$, $C_6H_{13}COO^-$, $C_7H_{15}COO^-$, $C_8H_{17}COO^-$, $C_9H_{19}COO^-$, $PhCOO^-$, $PhCH_2COO^-$ serve as anions.

Furthermore, salts of the following acids are possible: sulfuric acid, sulfonic acid, phosphoric acid, nitric acid, nitrous acid, perchloric acid, hydrobromic acid, hydrochloric acid, formic acid, acetic acid, propionic acid, succinic acid, oxalic acid, gluconic acid, (glyconic acid, dextronic acid), lactic acid, malic acid, tartaric acid, tartronic acid (hydroxymalonic acid, hydroxypropanedioic acid), fumaric acid, citric acid, ascorbic acid, maleic acid, malonic acid, hydroxymaleic acid, pyruvic acid, phenylacetic acid, (o-, m-, p-) toluic acid, benzoic acid, p-aminobenzoic acid, p-hydroxybenzoic acid, salicylic acid, p-aminosalicylic acid, methane sulfonic acid, ethane sulfonic acid, hydroxyethane sulfonic acid, ethylene sulfonic acid, p-toluenesulfonic acid, naphthylsulfonic acid, naphthylaminesulfonic acid, sulfanilic acid, camphorsulfonic acid, china acid, quinic acid, o-methyl-mandelic acid, hydrogen-benzenesulfonic acid, methionine, tryptophan, lysine, arginine, picric acid (2,4,6-trinitrophenol), adipic acid, d-o-tolyltartaric acid, glutaric acid.

In order to optimize the mechanical properties of the steel alloy, it is preferred that the composition is subjected to a heat treatment.

Adjustable parameters in the heat treatment are the temperature profile as well as the prevailing pressure and the gas composition. The temperature profile can be divided into the heating and cooling rates and into the holding times.

The parameters adjustable in the heat treatment and the parameters of the alloy interact in different ways with respect to the obtained result.

For example, a high nitrogen content increases the strength of the alloy so that this must be compensated by the heat treatment. The nitrogen content of the alloy also depends on the contents of the alloying elements which increase or reduce the solubility of nitrogen, this must be compensated by a pressure adaptation for adjusting the nitrogen content. Furthermore, the square root of the gas pressure is proportional to the resulting nitrogen content (Sievert's Law) and the solubility of nitrogen is a function of the temperature. Thus, the nitrogen content is dependent on the alloy composition, the process pressure and on the temperature.

Furthermore, the degree of the dislocation density has an impact on the grain formation rate and present micro precipitations affect the grain growth.

According to the exemplarily mentioned parameters that influence each other, it is evident that the heat treatment parameters must be adapted to the respective requirements.

Because of the low wall thickness of the stents, it is possible to generate a strong temperature gradient over time in the entire structural component.

In the heating phases temperature increments between 200° C. and 500° C. per minute are generated, and in the cooling phases temperature differences higher than 3000° C. and preferably higher than 5000° C. per minute are generated.

The maximal temperature of the structural component is in the range of 1050° C. to 1250° C. and the holding time is between 15 and 45 minutes.

The heat treatments are carried out under nitrogen atmosphere. The pressures were selected so that the desired nitrogen content in the alloy is achieved. The pressures used were in the range of 500 mbar to 2500 mbar.

The grain size in accordance with EN ISO 643 is defined herein as the average size of individual crystals within a metal or an alloy, in which the crystals are also referred to as grains. Herein, the grain size also influences the physical properties of the alloy: a fine-grained structure gives the alloy high strength and ductility.

A short heat treatment, as described above, produces a fine-grained structure. A fine-grained structure is of particular relevance due to the preferred material thicknesses of about 100 µm. A preferred grain size is at G=6-10, and particularly preferred at about G=7-8, which corresponds to approximately 7-10 grains per 100 µm.

The tensile strength $R_m$, refers to the limit at which the steel tears under load, so the maximal tensile stress of the steel. The tensile strength is determined by the tensile test. The tensile strength is referred to by the abbreviation $R_m$.

The elongation at break A is a characteristic value of the material that indicates the persistent extension of the sample after the break based on the initial length. The elongation at break characterizes the deformation capacity (or ductility) of a material. Herein, the ensued extension of a sample of the alloy after the break (in %) is indicated based on the original sample length.

It is preferred, if the elongation at break of the inventive steel alloy is larger than 60% and more preferably, if the elongation at break is larger than 65%.

The yield strength $R_p$ is herein defined as the tension at which after load relief a persistent elongation (=0.2% persistent deformation) is determined. The deformation measured is indicated as an index, the value used herein is 0.2% ($R_{p0.2}$).

It is preferred, when the yield strength $R_{p0.2}$ of the steel alloys generated by the above described heat treatment method is between 500 and 600 MPa.

Furthermore, it is preferred, if the tensile strength $R_m$ is between 900 and 1200 MPa.

The steel alloys according to the invention are particularly suitable as a material for the production of endoprostheses or stents.

Furthermore, the present invention therefore comprises a stent consisting of one of the steel alloys disclosed herein. The stent according to the invention preferably is a stent for blood vessels, urinary tracts, respiratory tracts, biliary tracts or the digestive tract. Again, among these stents the stents for blood vessels or more general for the cardiovascular system are especially preferred.

The stents are preferably cut from a tube, which consists of an iron alloy according to the invention, by means of a laser. Herein, stents are understood as lattice-shaped or mesh-shaped endoprostheses which are implanted into a hollow organ or a body cavity in order to keep it open. A stent is not a massive tube, but a mesh network. If one closely looks, for example, at a vascular stent, then this is cut out, e.g. by means of laser, from a massive tube, so that single struts as thin as possible result, which are connected to each other. The arrangement of the struts and nodes is called the stent design and can vary in accordance with the invention.

When cutting a stent, areas between the individual struts are cut out. An endoprosthesis therefore has a plurality of solid scaffolding components (e.g. struts in the form of rings, spirals, waves and wires), which altogether form the endoprosthesis, as well as a plurality of interstices between these solid components. Within the common embodiment of endoprostheses the struts merge in nodes. However, there are also embodiments of endoprostheses, where no or almost no nodes are present and the struts for example have the form of rings or spirals. Preferably the stents are self-expanding or balloon expandable stents, which are pushed by a catheter to the diseased area or to the area to be treated, where the stents are expanded to their defined nominal diameter.

The stents are cut from tubes, which consist of an alloy according to the invention, by means of a laser. The tubes are obtained by transformation of wires from the alloys according to the invention.

EXAMPLES

Example 1

Production of the Alloys

As raw materials for the manufacture of the master alloy purest starting materials are used and melted in a vacuum melting plant. Herein, all alloy components apart from nitrogen are added to the alloy in the appropriate amounts.

The primary material is remelted by means of DESU-method (pressure electro slag remelting procedure), whereat the nitrogen content is adjusted.

Example 2

Tube Production

From the alloys that have been produced as described in Example 1 a cast blank adapted to the extrusion press was heated before extrusion for 3-6 hours in a reducing atmosphere of nitrogen to 1100° C. to 1250° C. and cooled in air after the extrusion. The produced bars were drilled centrically hollow by means of a precision drilling method. Drawing steps followed, each with a subsequent heat treatment in a reducing atmosphere of nitrogen at 1100° C. to 1250° C., in which the tube was converted to the nominal size.

Example 3

Stent Fabrication

A tube produced according to Example 2 is fixed into an adapter in the laser machine. A pulsed solid state laser (FKL) cuts the contours of the stent design out of the tube. The laser cutting is performed under an inert gas atmosphere.

The stent design is stored in an NC program (numerical control). This provides the laser with the traverse paths, after which the tube is structured. By the laser beam cutting burr formation occurs, especially on the inside of the tube, along the entire cutting contour. This can cause that offcuts and cut-outs remain stuck in the contour after termination of the cutting process. The offcuts and cut-outs are mechanically removed and the stent is cleaned from manufacturing residues. In a first optical visual control an inspection of the cutting contour is performed.

In the following, the stent is electrochemically polished. The stent is anodically connected and immersed in an acid bath. Via a cathode fixed in the bath, an electric circuit is closed. The electric circuit is maintained for several minutes. The electropolishing is an inverted galvanic process where material is removed in a controlled manner from the surface of the anodically connected structural component. Due to the method removal takes preferably place at sharp corners and edges. The stent obtains a smooth surface and rounded edges along the contours. After polishing, the stent is cleaned and freed from acid residues. During the final cleaning all still remaining manufacturing residues are removed from the stent surface. In a last optical visual control the stent geometry is measured and the surface is tested on cleanliness.

Example 4

Determination of the Optimal Chromium Content in an Alloy According to the Invention For the determination of an optimally adjusted chromium content, the alloys A-I having the following compositions were produced according to Example 1:

|    | A    | B    | C    | D    | E    | F    | G    | H    | I    |
|----|------|------|------|------|------|------|------|------|------|
| Cr | 12.0 | 13.0 | 14.0 | 15.5 | 16.0 | 16.5 | 17.0 | 17.5 | 18.0 |
| Mn | 11   | 11   | 11   | 11   | 11   | 11   | 11   | 11   | 11   |
| Mo | 3.19 | 3.19 | 3.19 | 3.19 | 3.19 | 3.19 | 3.19 | 3.19 | 3.19 |
| N  | 0.62 | 0.62 | 0.62 | 0.62 | 0.62 | 0.62 | 0.62 | 0.62 | 0.62 |
| C  | 0.15 | 0.15 | 0.15 | 0.15 | 0.15 | 0.15 | 0.15 | 0.15 | 0.15 |
| Ni | 0.03 | 0.03 | 0.03 | 0.03 | 0.03 | 0.03 | 0.03 | 0.03 | 0.03 |
| Si | 0.33 | 0.33 | 0.33 | 0.33 | 0.33 | 0.33 | 0.33 | 0.33 | 0.33 |
| P  | 0.01 | 0.01 | 0.01 | 0.01 | 0.01 | 0.01 | 0.01 | 0.01 | 0.01 |

The corrosion behavior was determined on the basis of stents by means of potentiostatic tests.

The potentiostatic tests were carried out in an oxygen-free buffered physiological solution at 37° C. At first, the resting potential is determined. This means that a reference electrode and the structural component are immersed in the solution without applied voltage. A potential difference arises, which varies over time. Based on the potential difference, which appeared after one hour, an initial statement about the resistance of the alloy can be made. The more positive the value is the more resistant is the alloy.

Subsequently, a cyclic potentiodynamic polarization was carried out. For this, a potential difference between the structural component and the reference electrode was applied. The initial potential is selected so that it is 0.1 mV smaller than the resting potential arised. The applied potential is increased over time to for example 1.2 V and then reduced to the initial value, wherein the resulting current is measured. Based on the polarization curve, which is a voltage-current curve, the corrosion rates, the minimal currents, the breakdown potentials as well as the repassivation potentials can be determined. The parameters were determined according to ASTM F2129-10 with PBS (phosphate buffered saline).

For the alloys according to the invention corrosion rates between 15 and 25 nm/y (nanometer per year) were measured. For less resistant alloys corrosion rates of more than 50 nm/y were determined.

The determined breakdown potentials for the alloys according to the invention are between 1030 mV and 1070 mV. In contrast to this, the breakdown potential is reached already at 800 mV in the case of less resistant alloy compositions.

Even more important is the difference in the repassivation behavior which has a special meaning in the use as a stent. The alloys according to the invention have a repassivation potential from 940 to 960 mV, wherein alloys with a low repassivation potential reach only a repassivation potential from 100 to 150 mV.

The determined values—seen in isolation—have only little relevance, only the combination of good individual values result in a good corrosion behavior, wherein the weighting of the individual values depends on the case of application.

The alloys A and B have an uneven surface when polished. Viewed by light microscopy, the surface has slightly matt spots and does not appear high glossy in total. The corrosion resistance and in particular the repassivation potential are reduced compared to the alloys C to E.

The alloys C to E have a very good corrosion behavior. The chemical resistance is much higher than that of the material 1.4441 used for vascular stents. The breakdown and repassivation potentials are comparable with the material 2.4964 (L605).

The alloys C to E have an excellent polishability. A defect-free surface without measurable waviness and without indentations or ridges is produced. Viewed by light microscopy, there is a high glossy surface. The alloy F shows a good polishability, but the surface has isolated indentations, which are partially not polished. The corrosion behavior is still sufficient, similar to the material 1.4441.

The alloys G to I have an increasingly worse polishability with increasing chromium content. Polishing produces a wavy surface with non-polished indentations.

Potentiostatic tests of the alloys G to I show a reduced breakdown potential and a significantly reduced repassivation potential. The unexpected deterioration of the polishability and reduction of the corrosion resistance by increasing the chromium content is attributed to the formation of sigma phases and delta ferrite. Sigma phases and delta ferrite form at temperatures of about 600° C.-800° C. and could be caused by the heat treatment. Since the heat treatment must ensure a low yield strength, as well as a high ductility and a small grain of G>7, the formation of sigma phases and/or delta ferrite cannot be avoided for chromium contents higher than 16.5%. Thus, the chromium content should be limited to 16.5%. Due to the improvement of the corrosion and polishing properties chromium should also represent a minimum proportion of 14% of the alloy.

Example 5

Determination of the Optimal Manganese Content in an Alloy According to the Invention For the determination of an optimally adjusted manganese content, the alloys A-O having the following compositions were produced according to Example 1:

|    | A    | B    | C    | D    | E    | F    | G    | H    | I    | J    | K    | L    |
|----|------|------|------|------|------|------|------|------|------|------|------|------|
| Cr | 16.0 | 16.0 | 16.0 | 16.0 | 16.0 | 16.0 | 16.0 | 16.0 | 16.0 | 16.0 | 16.0 | 16.0 |
| Mn | 10   | 11   | 11.6 | 11.8 | 12   | 12.2 | 12.4 | 12.6 | 12.8 | 13   | 14   | 16   |
| Mo | 3.19 | 3.19 | 3.19 | 3.19 | 3.19 | 3.19 | 3.19 | 3.19 | 3.19 | 3.19 | 3.19 | 3.19 |
| N  | 0.62 | 0.62 | 0.62 | 0.62 | 0.62 | 0.62 | 0.62 | 0.62 | 0.62 | 0.62 | 0.62 | 0.62 |
| C  | 0.15 | 0.15 | 0.15 | 0.15 | 0.15 | 0.15 | 0.15 | 0.15 | 0.15 | 0.15 | 0.15 | 0.15 |
| Ni | 0.03 | 0.03 | 0.03 | 0.03 | 0.03 | 0.03 | 0.03 | 0.03 | 0.03 | 0.03 | 0.03 | 0.03 |
| Si | 0.33 | 0.33 | 0.33 | 0.33 | 0.33 | 0.33 | 0.33 | 0.33 | 0.33 | 0.33 | 0.33 | 0.33 |
| P  | 0.01 | 0.01 | 0.01 | 0.01 | 0.01 | 0.01 | 0.01 | 0.01 | 0.01 | 0.01 | 0.01 | 0.01 |

|    | M    | N    | O    |
|----|------|------|------|
| Cr | 16.0 | 16.0 | 16.0 |
| Mn | 18   | 20   | 22   |
| Mo | 3.19 | 3.19 | 3.19 |
| N  | 0.62 | 0.62 | 0.62 |
| C  | 0.15 | 0.15 | 0.15 |
| Ni | 0.03 | 0.03 | 0.03 |
| Si | 0.33 | 0.33 | 0.33 |
| P  | 0.01 | 0.01 | 0.01 |

The mechanical parameters yield strength $R_{p0.2}$, tensile strength $R_m$, and elongation at break (A) were determined in the tensile test on tube samples according to DIN EN 10002-1. For this, tube samples were mounted between two brackets. The brackets were fixed on the tensile testing machine and the tensile testing machine stretches the sample over the length up to the break. The mechanical parameters are calculated and put out by the machine based on the measured forces and distances and the given sample geometry.

The alloys A, B, C and D have a very good polishability. A very good surface quality without measurable waviness and without indentations or ridges is produced. Viewed by light microscopy, there is a defect-free high glossy surface. In particular the alloys A and B have in the polished state an excellent and absolutely defect-free high glossy surface viewed light microscopically.

The yield strengths are approximately 550 MPa for the alloy A and rise for the alloy D to approximately 600 MPa. The elongations at break of these alloys are up to over 65%.

The alloy E has a slightly worse polishability. Viewed by light microscopy, there is a glossy surface which is poor in defects. Sporadically, slight waviness of the surface is discernible by light microscopy. In part, there are also individual indentations existent in the structural component. The yield strength is about 610 MPa and the elongation at break of this alloy is around 60%.

With increasing manganese content, the alloys F, G, H and I have a polishability getting worse and worse. Viewed by light microscopy, there is a matt finished surface having defects. The surface is wavy. There are many indentations. Most of all, the alloys H and I have many non-polished indentations. The yield strength of alloy I rises up to approximately 640 MPa. With increasing manganese content the elongation at break is reduced to less than 60%.

The alloys J, K and L do not allow the production of polished surfaces according to the requirements that are put on stents. Viewed with the naked eye, the surfaces appear to be slightly matt, which is attributable to non-polished indentations. The yield strengths have values of up to over 760 MPa and the elongation at break is reduced to about 40%.

The alloys M, N and O do not allow the production of polished surfaces. Viewed with the naked eye, the surfaces appear to be matt, which is attributable to extensively present non-polished indentations. The yield strengths have values of up to over 850 MPa and the elongation at break is reduced to less than 35%.

Furthermore, the alloys P-S having the following compositions were produced according to Example 1:

|    | P    | Q    | R    | S    |
|----|------|------|------|------|
| Cr | 16.0 | 16.0 | 16.0 | 16.0 |
| Mn | 8.5  | 9.0  | 9.6  | 9.8  |
| Mo | 3.19 | 3.19 | 3.19 | 3.19 |
| N  | 0.62 | 0.62 | 0.62 | 0.62 |
| C  | 0.15 | 0.15 | 0.15 | 0.15 |
| Ni | 0.03 | 0.03 | 0.03 | 0.03 |
| Si | 0.33 | 0.33 | 0.33 | 0.33 |
| P  | 0.01 | 0.01 | 0.01 | 0.01 |

The alloys P and Q have a yield strength of approximately 500 MPa. Viewed by light microscopy, the surfaces have smaller indentations and sporadically also ridges after polishing. The elongation at break reaches values of about 50%.

The indentations after polishing suggest precipitation effects in the material. This is in accord with the reduced elongation at break compared to alloy A, because precipitations reduce the elongation at break. Since manganese increases the solubility of atomically dissolved nitrogen, precipitations can occur, if the manganese content is reduced at a constant nitrogen content.

After crimping and dilatation of the stent the alloy P has a slightly ferritic behavior. The chemical resistance of the alloy P is significantly reduced. The alloy Q has a reduced chemical resistance.

The yield strengths of the alloys R and S are about 540 MPa. The elongation at break reaches values of approximately 60%. Viewed by light microscopy, the surface quality of the alloys after polishing is high and poor in defects.

The chemical resistance in particular of alloy S is only reduced to a slight degree compared to alloy A.

The best surface quality and the highest elongation at break as well as the lowest yield strength are achieved with the alloys A-E, so that the manganese content of the inventive steel alloys is set to 10.0-12.0% by wt.

Example 6

Examination of the Impact of Molybdenum in an Alloy According to the Invention

For the examination of the impact of molybdenum on the mechanical and chemical properties of an alloy according to the invention, the alloys A-N having the following compositions were produced according to Example 1:

|    | A    | B    | C    | D    | E    | F    | G    | H    | I    | J    | K    | L    | M    | N    |
|----|------|------|------|------|------|------|------|------|------|------|------|------|------|------|
| Cr | 16.0 | 16.0 | 16.0 | 16.0 | 16.0 | 16.0 | 16.0 | 16.0 | 16.0 | 16.0 | 16.0 | 16.0 | 16.0 | 16.0 |
| Mn | 11   | 11   | 11   | 11   | 11   | 11   | 11   | 11   | 11   | 11   | 11   | 11   | 11   | 11   |
| Mo | 5.0  | 4.5  | 4.2  | 4.0  | 3.8  | 3.6  | 3.4  | 3.2  | 3.0  | 2.8  | 2.6  | 2.4  | 2.2  | 2.0  |
| N  | 0.62 | 0.62 | 0.62 | 0.62 | 0.62 | 0.62 | 0.62 | 0.62 | 0.62 | 0.62 | 0.62 | 0.62 | 0.62 | 0.62 |
| C  | 0.15 | 0.15 | 0.15 | 0.15 | 0.15 | 0.15 | 0.15 | 0.15 | 0.15 | 0.15 | 0.15 | 0.15 | 0.15 | 0.15 |
| Ni | 0.03 | 0.03 | 0.03 | 0.03 | 0.03 | 0.03 | 0.03 | 0.03 | 0.03 | 0.03 | 0.03 | 0.03 | 0.03 | 0.03 |
| Si | 0.33 | 0.33 | 0.33 | 0.33 | 0.33 | 0.33 | 0.33 | 0.33 | 0.33 | 0.33 | 0.33 | 0.33 | 0.33 | 0.33 |
| P  | 0.01 | 0.01 | 0.01 | 0.01 | 0.01 | 0.01 | 0.01 | 0.01 | 0.01 | 0.01 | 0.01 | 0.01 | 0.01 | 0.01 |

The alloys A and B have a poor polishability. Viewed by light microscopy, there is a matt-finished surface. The surface is wavy. There are both indentations and ridges. The elongation at break is between 35%-40%. The ridges can be explained by the formation of carbides, because these are ablated in a slowed manner during the polishing process. Likewise, the indentations can be attributed to carbides, because these leave indentations when they are detached from the material and fall out of the stent. The strongly reduced elongation at break in comparison to the alloys D to I can be attributed to the notch effect of carbides and to the carbon-depleted material in the surroundings of the carbides.

Potentiostatic tests show a higher flat ablation and a deteriorated repassivation behavior in comparison to the alloy D to I. This can be attributed to galvanic corrosion between carbides and the basic material.

The alloy C has a much better polish compared to the alloys A and B. There is a glossy surface, which has sporadically slight waviness. The elongation at break is above 50%.

The alloys D to I have an excellent polishability. A defect-free surface without measurable waviness and without indentations or ridges is produced. Viewed by light microscopy, there is a high glossy surface. The elongation at break of these alloys is up to over 65%.

The alloy J has a slightly worse polishability compared with alloy I. Viewed by light microscopy, there is a glossy surface which is poor in defects. Sporadically, slight waviness of the surface is discernible by light microscopy. In part, there are also individual indentations existent in the structural component. The elongation at break is around 50%.

Potentiostatic tests of alloy J, as described in example 4, showed a slightly reduced repassivation potential compared to the alloys D to I. The alloys K to N have an increasingly worse polishability with sinking molybdenum content. Polishing produces an uneven surface with non-polished indentations. Potentiostatic tests of the alloys K to N show a reduced breakdown potential and a significantly reduced repassivation potential.

The fundamental impact of molybdenum onto the corrosion resistance is evident from the MARC value. Molybdenum increases the chemical resistance 3.3 fold as much as chromium.

$$MARC = [\% \text{ Cr}] + 3.3 \times [\% \text{ Mo}] + 20 \times [\% \text{ C}] + 20 \times [\% \text{ N}] - 0.5 \times [\% \text{ Mn}] - 0.25 [\% \text{ Ni}]$$

The amount of molybdenum in the alloys according to the invention should, thus, be between 3.0% by wt. and 4.00% by wt.

Example 7

Examination of the Impact of Nitrogen on an Alloy According to the Invention

For the examination of the impact of nitrogen on the mechanical and chemical properties of an alloy according to the invention, the alloys A-L having the following compositions were produced according to Example 1:

|    | A    | B    | C    | D    | E    | F    | G    | H    | I    | J    | K    | L    |
|----|------|------|------|------|------|------|------|------|------|------|------|------|
| Cr | 16.0 | 16.0 | 16.0 | 16.0 | 16.0 | 16.0 | 16.0 | 16.0 | 16.0 | 16.0 | 16.0 | 16.0 |
| Mn | 11   | 11   | 11   | 11   | 11   | 11   | 11   | 11   | 11   | 11   | 11   | 11   |
| Mo | 3.19 | 3.19 | 3.19 | 3.19 | 3.19 | 3.19 | 3.19 | 3.19 | 3.19 | 3.19 | 3.19 | 3.19 |
| N  | 0.36 | 0.41 | 0.45 | 0.49 | 0.52 | 0.55 | 0.58 | 0.61 | 0.65 | 0.70 | 0.75 | 0.80 |
| C  | 0.15 | 0.15 | 0.15 | 0.15 | 0.15 | 0.15 | 0.15 | 0.15 | 0.15 | 0.15 | 0.15 | 0.15 |
| Ni | 0.03 | 0.03 | 0.03 | 0.03 | 0.03 | 0.03 | 0.03 | 0.03 | 0.03 | 0.03 | 0.03 | 0.03 |
| Si | 0.33 | 0.33 | 0.33 | 0.33 | 0.33 | 0.33 | 0.33 | 0.33 | 0.33 | 0.33 | 0.33 | 0.33 |
| P  | 0.01 | 0.01 | 0.01 | 0.01 | 0.01 | 0.01 | 0.01 | 0.01 | 0.01 | 0.01 | 0.01 | 0.01 |

The alloys A to D have a ferritic behavior and are therefore unsuitable as material for stents. Their corrosion resistances tested as described in Example 4 are extremely low. The alloy E has a much better corrosion behavior but the breakdown and repassivation potential is even lower than that of the samples F to I. An austenitic structure exists.

The alloys F to I have a very good corrosion behavior. The chemical resistance is much higher than that of the material 1.4441 used for vascular stents. The breakdown- and repassivation potentials are comparable with the material 2.4964 (L605).

The alloys A to H have a yield strength increasing with the nitrogen content from approximately 450 MPa to 600 MPa. The elongations at break of the samples A to D reach approximately 55%. The elongation at break of the samples E to J reaches approximately 65%. These parameters were obtained as described in Example 5.

The alloys I to L have a yield strength of up to approximately 640 MPa. The elongations at break reach values of 55%-65%. The alloy L has a higher corrosion rate and a lower repassivation potential. This is attributable to the formation of nitrides, which form at higher nitrogen contents and thus reduce the corrosion resistance by the depletion of chromium and nitrogen arising around the nitrides.

The dependence of the yield strength on the nitrogen content is evident from the following formula:

$$\text{Yield strength(MPa)} = 251 + 33 \times \text{Mn}(m\ \%) + 313 \times [\text{N} + \text{C}(m\ \%)]$$

Since the yield strength must be lower than 600 MPa for the use as a stent, a nitrogen content as low as possible is required in regard to the yield strength. In combination with the requirement of a fine grain of preferably G>7, this can only be produced up to a nitrogen content of maximally 0.7%.

The amount of nitrogen in the alloys according to the invention should thus be between 0.55% by wt. and 0.7% by wt.

Example 8

Examination of the Impact of Carbon on an Alloy According to the Invention

For the examination of the impact of carbon on the mechanical and chemical properties of an alloy according to the invention, the alloys A-L having the following compositions were produced according to Example 1:

|    | A | B | C | D | E | F | G | H | I | J | K | L |
|----|---|---|---|---|---|---|---|---|---|---|---|---|
| Cr | 16.0 | 16.0 | 16.0 | 16.0 | 16.0 | 16.0 | 16.0 | 16.0 | 16.0 | 16.0 | 16.0 | 16.0 |
| Mn | 11 | 11 | 11 | 11 | 11 | 11 | 11 | 11 | 11 | 11 | 11 | 11 |
| Mo | 3.19 | 3.19 | 3.19 | 3.19 | 3.19 | 3.19 | 3.19 | 3.19 | 3.19 | 3.19 | 3.19 | 3.19 |
| N  | 0.62 | 0.62 | 0.62 | 0.62 | 0.62 | 0.62 | 0.62 | 0.62 | 0.62 | 0.62 | 0.62 | 0.62 |
| C  | 0.02 | 0.05 | 0.1 | 0.12 | 0.14 | 0.16 | 0.18 | 0.20 | 0.22 | 0.24 | 0.26 | 0.28 |
| Ni | 0.03 | 0.03 | 0.03 | 0.03 | 0.03 | 0.03 | 0.03 | 0.03 | 0.03 | 0.03 | 0.03 | 0.03 |
| Si | 0.33 | 0.33 | 0.33 | 0.33 | 0.33 | 0.33 | 0.33 | 0.33 | 0.33 | 0.33 | 0.33 | 0.33 |
| P  | 0.01 | 0.01 | 0.01 | 0.01 | 0.01 | 0.01 | 0.01 | 0.01 | 0.01 | 0.01 | 0.01 | 0.01 |

The alloys A-C have a low corrosion resistance, measured as described in Example 4. Particularly the capability of repassivation is reduced in comparison to the alloys D-H. The alloys have a low proportion of delta ferrite. In the alloy C delta ferrite can be found only sporadically. The elongation at break is approximately 55%-60% and the yield strength is approximately 550-570 MPa.

The alloys D-J have no delta ferrite. The alloy D has a higher corrosion resistance than the alloys A-C. The capability of repassivation is reduced in comparison to the alloys E-H.

The alloys E-H have a very high corrosion resistance with a high repassivation potential. The elongation at break and uniform elongation are increased in comparison to the other alloys. The elongation at break is up to over 65%. The yield strength is approximately 570-600 MPa.

The alloy I has a high corrosion resistance. Most notably, the repassivation potential is reduced compared to the alloys E-H. This is attributable to the formation of scattered chromium carbides.

The alloy J has a significantly reduced corrosion resistance which can be explained by the formation of chromium carbides. The yield strengths of the alloys I-L are approximately at 620-640 MPa. The corrosion resistance of the alloys K and L is reduced even further.

The amount of carbon in the alloys according to the invention should therefore be between 0.10% by wt. and 0.20% by wt.

Example 9

Examination of the Impact of Carbon and Nitrogen on an Alloy According to the Invention For the examination of the impact of carbon in dependence on the nitrogen content on the mechanical properties of an alloy according to the invention, the alloys A-I1 having the following compositions were produced according to Example 1:

|    | A | B | C | D | E | F | G | H | I | J | K | L |
|----|---|---|---|---|---|---|---|---|---|---|---|---|
| Cr | 16.0 | 16.0 | 16.0 | 16.0 | 16.0 | 16.0 | 16.0 | 16.0 | 16.0 | 16.0 | 16.0 | 16.0 |
| Mn | 11 | 11 | 11 | 11 | 11 | 11 | 11 | 11 | 11 | 11 | 11 | 11 |
| Mo | 3.19 | 3.19 | 3.19 | 3.19 | 3.19 | 3.19 | 3.19 | 3.19 | 3.19 | 3.19 | 3.19 | 3.19 |
| N  | 0.50 | 0.6 | 0.7 | 0.8 | 0.9 | 0.50 | 0.6 | 0.7 | 0.8 | 0.9 | 0.50 | 0.6 |
| C  | 0.08 | 0.08 | 0.08 | 0.08 | 0.08 | 0.12 | 0.12 | 0.12 | 0.12 | 0.12 | 0.16 | 0.16 |
| Ni | 0.03 | 0.03 | 0.03 | 0.03 | 0.03 | 0.03 | 0.03 | 0.03 | 0.03 | 0.03 | 0.03 | 0.03 |
| Si | 0.33 | 0.33 | 0.33 | 0.33 | 0.33 | 0.33 | 0.33 | 0.33 | 0.33 | 0.33 | 0.33 | 0.33 |
| P  | 0.01 | 0.01 | 0.01 | 0.01 | 0.01 | 0.01 | 0.01 | 0.01 | 0.01 | 0.01 | 0.01 | 0.01 |

|    | M | N | O | P | Q | R | S | T | U | V | W |
|----|---|---|---|---|---|---|---|---|---|---|---|
| Cr | 16.0 | 16.0 | 16.0 | 16.0 | 16.0 | 16.0 | 16.0 | 16.0 | 16.0 | 16.0 | 16.0 |
| Mn | 11 | 11 | 11 | 11 | 11 | 11 | 11 | 11 | 11 | 11 | 11 |
| Mo | 3.19 | 3.19 | 3.19 | 3.19 | 3.19 | 3.19 | 3.19 | 3.19 | 3.19 | 3.19 | 3.19 |
| N  | 0.7 | 0.8 | 0.9 | 0.50 | 0.6 | 0.7 | 0.8 | 0.50 | 0.6 | 0.7 | 0.8 |
| C  | 0.16 | 0.16 | 0.16 | 0.20 | 0.20 | 0.20 | 0.20 | 0.24 | 0.24 | 0.24 | 0.24 |
| Ni | 0.03 | 0.03 | 0.03 | 0.03 | 0.03 | 0.03 | 0.03 | 0.03 | 0.03 | 0.03 | 0.03 |
| Si | 0.33 | 0.33 | 0.33 | 0.33 | 0.33 | 0.33 | 0.33 | 0.33 | 0.33 | 0.33 | 0.33 |
| P  | 0.01 | 0.01 | 0.01 | 0.01 | 0.01 | 0.01 | 0.01 | 0.01 | 0.01 | 0.01 | 0.01 |

|    | X | Y | Z | A1 | B1 | C1 | D1 | E1 | F1 | G1 | H1 | I1 |
|----|---|---|---|----|----|----|----|----|----|----|----|----|
| Cr | 16.0 | 16.0 | 16.0 | 16.0 | 16.0 | 16.0 | 16.0 | 16.0 | 16.0 | 16.0 | 16.0 | 16.0 |
| Mn | 11 | 11 | 11 | 11 | 11 | 11 | 11 | 11 | 11 | 11 | 11 | 11 |
| Mo | 3.19 | 3.19 | 3.19 | 3.19 | 3.19 | 3.19 | 3.19 | 3.19 | 3.19 | 3.19 | 3.19 | 3.19 |
| N  | 0.50 | 0.6 | 0.7 | 0.8 | 0.50 | 0.6 | 0.7 | 0.8 | 0.5 | 0.6 | 0.7 | 0.80 |

-continued

| | | | | | | | | | | | | |
|---|---|---|---|---|---|---|---|---|---|---|---|---|
| C | 0.30 | 0.30 | 0.30 | 0.30 | 0.36 | 0.36 | 0.36 | 0.36 | 0.40 | 0.40 | 0.40 | 0.40 |
| Ni | 0.03 | 0.03 | 0.03 | 0.03 | 0.03 | 0.03 | 0.03 | 0.03 | 0.03 | 0.03 | 0.03 | 0.03 |
| Si | 0.33 | 0.33 | 0.33 | 0.33 | 0.33 | 0.33 | 0.33 | 0.33 | 0.33 | 0.33 | 0.33 | 0.33 |
| P | 0.01 | 0.01 | 0.01 | 0.01 | 0.01 | 0.01 | 0.01 | 0.01 | 0.01 | 0.01 | 0.01 | 0.01 |

The alloys A and B have a low corrosion resistance. Particularly, the repassivation potential is reduced. The elongation at break is approximately 55%-60% and the yield strength is approximately 530-560 MPa. The alloy C has a sufficient chemical resistance with a slightly reduced repassivation potential. The elongation at break is approximately 60% and the yield strength is approximately 600 MPa. The alloys D-E have a good chemical resistance. The elongation at break is approximately 55% and the yield strength is approximately 620-650 MPa.

The alloy F has a good corrosion behavior with a high repassivation potential. In total, the chemical resistance is slightly inferior to the alloys G-H. The elongation at break is approximately 60% and the yield strength is approximately 550 MPa. The alloys G-H have a very good chemical resistance. The elongation at break is approximately 60%-65% and the yield strength is approximately 580-600 MPa. The alloys I-J have a reduced chemical resistance. The elongation at break is approximately 55%-60% and the yield strength is approximately 620-660 MPa.

The alloy K has a good chemical resistance with a high repassivation potential. In total, the chemical resistance is slightly inferior to the alloys L-M. The elongation at break is approximately 60% and the yield strength is approximately 560 MPa. The alloys L-M have a very good chemical resistance with a high repassivation potential. The elongation at break is approximately 65% and the yield strength is approximately 590-610 MPa. The alloy N has a reduced chemical resistance with a reduced repassivation potential. The elongation at break is approximately 55% and the yield strength is approximately 640 MPa.

The alloy O has a clearly reduced chemical resistance with a low repassivation potential. The elongation at break is approximately 50% and the yield strength is approximately 660 MPa.

The alloys P-Q have a sufficient chemical resistance with a high repassivation potential. The elongation at break is approximately 60% and the yield strength is approximately 570-600 MPa. The alloy R has a very good chemical resistance with a high repassivation potential. The elongation at break is approximately 65% and the yield strength is approximately 630 MPa. The alloy S has a higher corrosion rate with a low repassivation potential. The elongation at break is approximately 60% and the yield strength is approximately 670 MPa.

The alloys T-U have a still sufficient chemical resistance with a sufficient repassivation potential. The elongation at break is approximately 60% and the yield strength is approximately 590-620 MPa. The alloys V-W have a reduced chemical resistance with a reduced repassivation potential. The elongation at break is approximately 55% and the yield strength is approximately 660-690 MPa.

The alloys X-Y have a reduced chemical resistance in comparison to alloy G. The repassivation potential is also reduced. The elongation at break reaches values of about 55%. The yield strength is 610-640 MPa. The alloys Z-A1 have an even further reduced chemical resistance. The elongation at break is approximately 50%. The yield strength reaches values of 670-700 MPa. The polished surfaces show indentations to an increased degree.

The alloys B1-C1 have a clearly reduced chemical resistance also in regard to the repassivation potential. The elongation at break reaches values of 50-55%. The yield strength is at 620-650 MPa. The polished surfaces show indentations to an increased degree, which points to fine precipitation events.

The alloys D1-E1 have a low chemical resistance and are thus not to be used as a stent material. The elongation at break is 45-50%. The yield strength reaches values of 680-710 MPa. The polished surfaces, especially of alloy E1, show larger indentations to an increased degree. Precipitation effects occur.

The alloys F1-G1 have a strongly reduced chemical resistance and are thus not applicable as stent material. The elongation at break is 45-50%. The yield strength reaches values of 640-670 MPa. Indentations but also ridges are present to an increased degree in the polished state, which are a consequence of precipitations.

The alloys H1-I1 are chemically not resistant. The alloys have a low breakdown- and repassivation potential. The elongation at break is approximately 40%. The yield strength reaches values of 690-720 MPa. The alloys H1-I1 have after polishing no polished surfaces that are suitable for the use as a stent.

The alloys G and H as well as L and M and R show a special applicability as stent material due to the combination of positive properties. They all have a nitrogen content between 0.6% and 0.7%, a carbon content between 0.12% and 0.2% and a ratio of N:C of 3.50 to 5.83.

The invention claimed is:

1. A stent consisting of a steel alloy consisting of the following components based on the total weight of the alloy:

| | |
|---|---|
| 14.0% by wt.-16.5% by wt. | chromium |
| 10.0% by wt.-12.0% by wt. | manganese |
| 3.0% by wt.-4.0% by wt. | molybdenum |
| 0.55% by wt.-0.70% by wt. | nitrogen |
| 0.10% by wt.-0.20% by wt. | carbon |
| 1 ppm-2.0% by wt. | impurities such as other metals, semimetals, metal salts and non-metals | the rest up to 100% by wt. is iron.

2. The stent consisting of a steel alloy according to claim 1 consisting of:
   1 ppm-2.0% by wt. impurities in form of other metals in a maximal amount of each up to 0.075% by wt. and non-metals from the group S, Si, P in a maximal total amount of 1.2% by wt.

3. The stent consisting of a steel alloy according to one of the claim 1 or 2 additionally consisting of:
   0.00% by wt.-0.05% by wt. nickel.

4. The stent consisting of a steel alloy according to claim 1 additionally consisting of:
   0.00% by wt.-1.00% by wt. silicon.

5. The stent consisting of a steel alloy according to claim 1 which has been subjected to a heat treatment.

6. The stent consisting of a steel alloy according to claim 1, having a yield strength $R_{p0.2}$ between 500 and 600 MPa.

7. The stent consisting of a steel alloy according to claim 1, having a grain size G between 6 and 10.

8. The stent consisting of a steel alloy according to claim 1, for blood vessels, urinary tracts, respiratory tracts, biliary tracts or the digestive tract.

* * * * *